United States Patent [19]

Etzbach

[11] Patent Number: 4,980,495

[45] Date of Patent: Dec. 25, 1990

[54] TRIALKYLAMINE SALTS OF 3-CHLORO-1,1-DICYANO-2-HYDROXY-1-PROPENE AND PREPARATION OF 2-AMINO-4-CHLORO-3-CYANO-5-FORMYL-THIOPHENE

[75] Inventor: Karl-Heinz Etzbach, Frankenthal, Fed. Rep. of Germany

[73] Assignee: BASF Aktiengesellschaft, Ludwigshafen, Fed. Rep. of Germany

[21] Appl. No.: 462,971

[22] Filed: Jan. 5, 1990

Related U.S. Application Data

[63] Continuation of Ser. No. 272,423, Nov. 17, 1988, abandoned.

[30] Foreign Application Priority Data

Nov. 17, 1987 [DE] Fed. Rep. of Germany ....... 3738910

[51] Int. Cl.$^5$ ............................................ C07C 255/00
[52] U.S. Cl. ...................................... 558/451; 549/61
[58] Field of Search .......................... 549/61; 558/451

[56] References Cited

FOREIGN PATENT DOCUMENTS 193885 9/1986 European Pat. Off. .
3519455 12/1986 Fed. Rep. of Germany ........ 549/61

*Primary Examiner*—Alan Siegel
*Attorney, Agent, or Firm*—Oblon, Spivak, McClelland, Maier & Neustadt

[57] ABSTRACT

Trialkylamine salts of 3-chloro-1,1-dicyano-2-hydroxy-1-propene, where the trialkylamine has from 10 to 24 carbon atoms, a process for their preparation from malononitrile, chloroacetyl chloride, and a trialkylamine, and a process for the preparation of 2-amino-4-chloro-3-cyano-5-formylthiophene in which a trialkylamine salt of 3-chloro-1,1-dicyano-2-hydroxy-1-propene is cyclized with hydrogen sulfide or another sulfide and treated with a mixture of N,N-dimethylformamide and phosphoryl chloride, and the product is hydrolyzed by acid without being isolated previously.

3 Claims, No Drawings

TRIALKYLAMINE SALTS OF 3-CHLORO-1,1-DICYANO-2-HYDROXY-1-PROPENE AND PREPARATION OF 2-AMINO-4-CHLORO-3-CYANO-5-FORMYLTHIOPHENE

This application is a continuation of application Ser. No. 272,423, filed on Nov. 17, 1988, now abandoned.

The present invention relates to trialkylamine salts of 3-chloro-1,1-dicyano-2-hydroxy-1-propene, where the trialkylamine has from 10 to 24 carbon atoms, a process for their preparation from malononitrile, chloroacetyl chloride, and a trialkylamine, and a process for the preparation of 2-amino-4-chloro-3-cyano-5-formylthiophene in which a trialkylamine salt of 3-chloro-1,1-dicyano-2-hydroxy-1-propene is cyclized with hydrogen sulfide or another sulfide and treated with a mixture of N,N-dimethylformamide and phosphoryl chloride, and the product is hydrolyzed by acid without being isolated previously.

The preparation of 2-amino-4-chloro-3-cyano-5-formylthiophene is known from EP-A-No. 193 885, according to which the intermediate triethylamine salt of 3-chloro-1,1-dicyano-2-hydroxy-1-propene is prepared from malononitrile, chloroacetyl chloride, and triethylamine and cyclized with ammonium sulfide to 2-amino-3-cyano-4-hydroxythiophene, which is then treated with a mixture of N,N-dimethylformamide and phosphoryl chloride; the N'-(4-chloro-3-cyano-5-formyl-2-thienyl)-N,N-dimethylformamidine that is formed is isolated and then hydrolyzed with formic acid, giving the required product. However, it has been found that the yield of 2-amino-4-chloro-3-cyano-5-formylthiophene obtained by this process is unsatisfactory.

The aim of the present invention was to provide novel intermediates from which 2-amino-4-chloro-3-cyano-5-formylthiophene could be obtained in better yield.

We have found trialkylamine salts of 3-chloro-1,1-dicyano-2-hydroxy-1-propene, where the trialkylamine has from 10 to 24 carbon atoms. These salts, of the general formula (I),

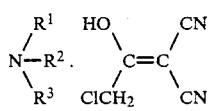

where $R^1$, $R^2$, and $R^3$ are identical or different alkyls, each of any number of carbon atoms from 1 to 22 provided that the total number is from 10 to 24, are suitable and advantageous for the preparation of 2-amino-4-chloro-3-cyano-5-formylthiophene (II).

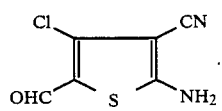

Suitable trialkylamines for the novel salts include tributylamine, tripentylamine, trihexylamine, tris(2-ethylhexyl)amine, N,N-dimethyl-(2-ethylhexyl)amine, and N-methylbis(2-ethylhexyl)amine.

Those trialkylamine salts of 3-chloro-1,1-dicyano-2-hydroxy-1-propene are preferred in which the trialkylamine has from 10 to 17 carbon atoms, in particular 12 carbon atoms. The tributylamine salt is to be accorded especial preference.

The novel trialkylamine salts of 3-chloro-1,1-dicyano-2-hydroxy-1-propene are obtained conveniently by the simultaneous reaction of malononitrile, chloroacetyl chloride, and the appropriate trialkylamine. The reaction takes place at a temperature of from $-10°$ C. to $100°$ C., preferably from $0°$ C. to $20°$ C., in an inert organic solvent, for example in N,N-dimethylformamide, N-methyl-2-pyrrolidone, dioxane, tetrahydrofuran, methylene chloride, or tert-butyl methyl ether; N,N-dimethylformamide is the solvent of choice. In general the mole ratio of malononitrile to chloroacetyl chloride to trialkylamine is from 1:1:2 to 1:1.5:3.

In the novel process it is expedient to add chloroacetyl chloride and trialkylamine, simultaneously, but from separate vessels, to a solution of malononitrile in the organic solvent while maintaining the required temperature. The reaction mixture is stirred for a further period, generally for from 0.1 h to 1 h, then run into cold dilute hydrochloric acid. Finally, the acid mixture is extracted with ether, the ether phase is dried, and the solvents are removed.

Unlike triethylamine, the trialkylamines on which the novel salts are based can be recovered when the thiophene is prepared.

It is surprising that the novel trialkylamine salts of general formula (I) are insoluble in water and dilute mineral acids and can therefore be isolated. They are formed in good yields and high purity, moreover they are thermally stable to a high degree. These salts are eminently suitable intermediates for the synthesis of 2-amino-4-chloro-3-cyano-5-formylthiophene or other heterocyclic compounds, which are themselves valuable as intermediates for the manufacture of dyes.

We have also found that advantageous results are obtained in the preparation of 2-amino-4-chloro-3-cyano-5-formylthiophene by cyclization of 3-chloro-1,1-dicyano-2-hydroxy-1-propene with hydrogen sulfide or another sulfide, treatment of the resulting 2-amino-3-cyano-4-hydroxythiophene with a mixture of N,N-dimethylformamide and phosphoryl chloride, and acid hydrolysis of the N'-(4-chloro-3-cyano-5-formyl-2-thienyl)-N,N-dimethylformamidine so formed, when a salt of 3-chloro-1,1-dicyano-2-hydroxy-1-propene and a trialkylamine having from 10 to 24 carbon atoms is cyclized and the N'-(4-chloro-3-cyano-5-formyl-2-thienyl)-N,N-dimethylformamidine is subjected to acid hydrolysis without its having been isolated previously. 2-Amino-3-cyano-4-hydroxythiophene (III)

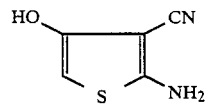

is prepared by cyclizing the novel trialkylamine salts of general formula (I) with hydrogen sulfide or another sulfide. Suitable sulfides are the sulfides or hydrogensulfides of alkali and alkaline earth metals, for instance sodium or potassium sulfide or hydrogensulfide and calcium sulfide or hydrogensulfide, and ammonium sulfide or hydrogen sulfide. The mole ratio of trialkylamine salt (I) to hydrogen sulfide (or sulfide) is from 1:1 to 1:2 as a rule.

The cyclization reaction is preferably carried out in water at a temperature of from $0°$ C. to $80°$ C. When it is finished, generally after from 1 h to 4 h, dilute hydrochloric acid is added and the 4-hydroxythiophene derivative (III) is separated, washed, and dried.

The intermediate N'-(4-chloro-3-cyano-5-formyl-2-thienyl)-N,N-dimethylformamidine (IV)

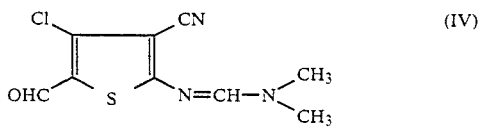

is formed from the 4-hydroxythiophene derivative (III) by treatment with a mixture of N,N-dimethylformamide and phosphoryl chloride and then converted direct to 2-amino-4-chloro-3-cyano-5-formylthiophene by acid hydrolysis, without its having been isolated. For this it is expedient to dissolve the 4-hydroxythiophene derivative (III) in N,N-dimethylformamide and add phosphoryl chloride to the solution at a temperature of from 20° C. to 80° C.; the mole ratio of the hydroxythiophene to N,N-dimethylformamide to phosphoryl chloride is generally from 1:10:2 to 1:20:3. After a further period of from 2 h to 8 h, during which the solution is kept stirred at a temperature of from 20° C. to 80° C., the formamidine (IV) that is formed is subjected to acid hydrolysis, which is done conveniently by running the reaction mixture into water. After completion of the latter procedure (which is accompanied by a strongly exothermic reaction) the mixture is usually stirred at a temperature of from 80° C. to 100° C. for from 1 h to 4 h, during which time the required thiophene derivative (II) precipitates. The product is finally separated, washed, and dried.

The novel process gives yields considerably higher than those given by the method disclosed in EP-A-No. 193 885, and in addition the formamidine (IV) does not have to be isolated.

As mentioned above, 2-amino-4-chloro-3-cyano-5-formylthiophene is a valuable intermediate for the synthesis of azo dyes.

The following examples provide some details of the invention.

EXAMPLE 1

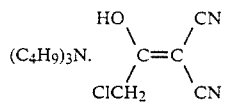

To a solution of 33 g of malononitrile in 100 ml of N,N-dimethylformamide were added simultaneously from separate vessels 56.5 g of chloroacetyl chloride and 185 g of tributylamine at a temperature of 0° C. The mixture was stirred for a further 15 min at 0° C., then poured into 500 ml of ice-cold dilute hydrochloric acid. The mixture was extracted with three portions of ether and the combined extracts were washed with water and dried over sodium sulfate.

The ether was taken off under reduced pressure, giving 123 g (75% yield) of the tributylamine salt of 3-chloro-1,1-dicyano-2-hydroxy-1-propene as an orange oil.

IR spectrum (film): peaks at 2963 cm$^{-1}$, 2937 cm$^{-1}$, 2876 cm$^{-1}$ (C-H), 2203 cm$^{-1}$, 2182 cm$^{-1}$ (CN), and 1571 cm$^{-1}$ (C = O)

| For $C_{17}H_{30}ClN_3O$ (M = 327.5 g/mol) | | | | | |
|---|---|---|---|---|---|
| | C | H | Cl | N | O |
| Required | 62.27 | 9.22 | 10.81 | 12.81 | 4.88% |
| Found | 61.8 | 9.1 | 11.1 | 12.9 | 5.3% |

The salts of N,N-dimethyl-(2-ethylhexyl)amine, tris(2-ethylhexyl)amine, and tripentylamine were obtained similarly.

EXAMPLE 2 (comparison)

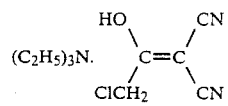

In the way described in Example 1 33 g of malononitrile, 56.5 g of chloroacetyl chloride, and 101 g of triethylamine reacted together in 100 ml of N,N-dimethylformamide. When the reaction mixture was added to dilute hydrochloric acid the triethylamine salt that was formed remained in solution and could not be isolated.

EXAMPLE 3

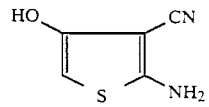

A mixture of 9.5 g of the tributylamine salt from Example 1, 2.9 g of 60% by weight sodium sulfide, and 100 ml of water was stirred for 4 h at room temperature, then acidified with dilute hydrochloric acid.

The resulting precipitate was filtered off, washed with water, and dried; this gave 2.5 g (89% yield) of 2-amino-3-cyano-4-hydroxythiophene, m.p. >300° C.

EXAMPLE 4

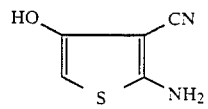

To a solution of 231 g of malononitrile in 350 ml of N,N-dimethylformamide were added simultaneously from separate vessels 396 g of chloroacetyl chloride and 1295 g of tributylamine at a temperature of 0° C. The mixture was stirred for a further 15 min at 0° C., then added to a mixture of 455 g of 60% by weight sodium sulfide, 1000 g of ice, and 1000 ml of water.

The resulting mixture was stirred for 3 h, then the product was filtered off, washed successively with water, dilute hydrochloric acid, and again water, and dried; this gave 425 g (87% yield) of 2-amino-3-cyano-4-hydroxythiophene, m.p. >300° C.

EXAMPLES 5-7

Examples 5-7 were carried out in the way described in Example 4, but with only a seventh of the amounts of starting compounds and amines other than tributylamine.

EXAMPLE 5

Amine used: 157 g of N,N-dimethyl-(2-ethylhexyl)amine.

Yield of 2-amino-3-cyano-4-hydroxythiophene: 58 g (83%).

EXAMPLE 6

Amine used: 354 g of tris(2-ethylhexyl)amine.

Yield of 2-amino-3-cyano-4-hydroxythiophene: 56.3 g (80%).

EXAMPLE 7

Amine used: 227 g of tripentylamine.

Yield of 2-amino-3-cyano-4-hydroxythiophene: 58.9 g (84%).

EXAMPLE 8

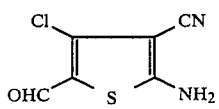

To 280 g of 2-amino-3-cyano-4-hydroxythiophene dissolved in 1800 ml of N,N-dimethylformamide was added within a period of 30 min 612 g of phosphoryl chloride, the temperature being kept at from 70° C. to 80° C. by cooling with water. The mixture was stirred for a further 2 h at 80° C., then run into 1800 ml of water; the temperature of the resulting ebullient mixture rose to about 110° C. When the exothermic reaction ceased the mixture was boiled for a further 1 h, during which time the required product precipitated.

After the mixture had cooled to room temperature the product was filtered off, washed with water, and dried; this gave 317 g (85% yield) of 2-amino-4-chloro-3-cyano-5-formylthiophene, m.p. 270° C.

I claim:

1. Trialkylamine salts of 3-chloro-1,1-dicyano-2-hydroxy-1-propene having the formula:

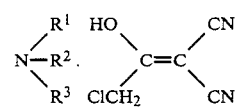

wherein $R^1$, $R^2$ and $R^3$, which are identical or different alkyl groups, each have from 1 to 22 carbon atoms, provided that the total number of carbon atoms is from 10 to 24.

2. The trialkylamine salts according to claim 1, wherein the total number of carbon atoms of $R^1$, $R^2$ and $R^3$ is from 10 to 17 carbon atoms.

3. The trialkylamine salts according to claim 1, wherein said trialkylamine salt is the tributylamine salt.

* * * * *